(12) United States Patent
Barberio

(10) Patent No.: US 6,547,751 B1
(45) Date of Patent: Apr. 15, 2003

(54) SURGICAL CAST VENTING DEVICE USING STRETCHABLE NET MATERIAL

(76) Inventor: Alessandro Barberio, Suite 205, 4325 Steeles Ave., West North York, Ontario M3N 1V7 (CA)

( * ) Notice: Subject to any disclaimer, the term of this patent is extended or adjusted under 35 U.S.C. 154(b) by 0 days.

(21) Appl. No.: 09/476,106

(22) Filed: Jan. 3, 2000

(51) Int. Cl.⁷ .................................................. A61F 5/00
(52) U.S. Cl. ...................................................... 602/14
(58) Field of Search .............................. 602/3, 14, 10, 602/76, 79, 60, 61

(56) References Cited

U.S. PATENT DOCUMENTS

| | | |
|---|---|---|
| 1,213,941 A | 1/1917 | Patrick |
| 2,480,035 A | 8/1949 | Lindstrom |
| 2,666,207 A | 1/1954 | Lucas |
| 2,704,067 A | 3/1955 | Moses |
| 2,731,963 A | 1/1956 | Blank |
| 2,822,806 A | 2/1958 | Blank |
| 3,116,731 A | 1/1964 | Baxter |
| 3,307,537 A | 3/1967 | Simon |
| 3,417,408 A | 12/1968 | Caggiano |
| 3,656,477 A | 4/1972 | Thomas |
| 3,701,349 A | 10/1972 | Larson |
| 3,882,857 A | 5/1975 | Woodall, Jr. |
| 3,930,496 A | 1/1976 | Gibbons |
| 3,998,220 A | 12/1976 | Cleer, Jr. |
| 4,308,862 A | 1/1982 | Kalmar |
| 4,387,710 A | 6/1983 | Beatty |
| 4,898,160 A | 2/1990 | Brownlee |
| 5,086,518 A | 2/1992 | Staley |
| 5,226,194 A | 7/1993 | Staley |
| 5,511,323 A | 4/1996 | Dahlgren |

*Primary Examiner*—Kim M. Lewis
(74) *Attorney, Agent, or Firm*—Ridout & Maybee

(57) ABSTRACT

A surgical cast venting device including a stretchable piece of fabric material and one or more aerating devices affixed to and located on the inner surface of the material. The preferred fabric material is stretchable and porous and can have a flexible tubular configuration with two opposite ends which are open. The preferred aerating devices are elongate tubular members which are open at both ends and perforated along their length. These members can be affixed to the fabric material by means of a medical adhesive. The venting device is adapted for placement around part of a human body or animal body prior to application of a surgical cast. In a preferred version, the tubular members extend in a longitudinal direction relative to the longitudinal axis of the fabric.

13 Claims, 20 Drawing Sheets

SURGICAL CAST VENTING DEVICE USING STRETCHABLE NET MATERIAL

BACKGROUND OF THE INVENTION

This invention relates to devices for venting a surgical cast to be applied to the body of a human or animal.

A variety of different structures and methods have been proposed in the past for providing air ventilation to the skin under a surgical cast. It is known, for example, to provide cast venting devices in the form of a woven fabric with an elongate tube or other such air passageway in contact with the skin and over which the plaster of paris mix casting material can be placed to form the cast. Also, it is known to provide a device for forcing air under the cast, which device may comprise an air pump.

In the applicant's pending Canadian patent application serial No. 2,254,492 filed Nov. 25, 1998, there is described a surgical cast venting device which comprises an elongate porous woven fabric strip together with a number of flexible, elongate tubes with holes distributed along their respective lengths. These tubes are distributed along the length of and attached to the fabric strip on one side thereof. Each tube extends lengthwise in a direction substantially parallel to this one side. The elongate strip is suitable for winding around part of a human body prior to application of a surgical cast. Although this venting device works satisfactorily, it may be somewhat difficult for some users to use over part of the body that is bent, for example, an elbow or knee. Furthermore, some skill may be required on the part of the medical technician or doctor who is applying this venting device in order to ensure that the device is applied correctly and without undesirable gaps in the device after it has been mounted on the person's body part or limb.

U.S. Pat. No. 3,656,477 which issued Apr. 18, 1972 to Bobby Thomas et al. describes a ventilation device for use with a medical cast, this device including a stockinette with a series of air vent units secured thereto and arranged at holes formed in the stockinette material. The air vent units are arranged in staggered relationship along rows and are arranged so as to extend through the plaster of paris forming the cast. These air vent units are mounted on the exterior of the stockinette material, which may be in the form of a cylindrical sock.

Earlier U.S. Pat. No. 2,666,207 issued Jan. 19, 1954 to A. Lucas describes a ventilated stocking intended for use inside a shoe or boot and not for use within a medical cast. This known stocking has the configuration of a standard stocking and is open at one end only. Mounted in the stocking material are a number of resilient tubular elements which may be made of rubber or plastic. These elements, which do not extend the length of the stocking, are only open at their opposite ends and they are woven into the stocking material itself.

More recent U.S. Pat. No. 3,307,537 issued Mar. 7, 1967 to G. B. Simon et al. describes a laminated orthopedic cast that includes an inner lamina of soft woven fabric that can be stretched, a central barrier lamina of stretchable material, this lamina being impervious to liquid resin and bonded to the outer surface of the inner lamina, and an outer lamina of fiberglass fabric. The outer lamina is permeated with air dried polyester resin for bonding its inner surface to the outer surface of the inner lamina and rigidizing the cast. This known cast device includes a number of spaced tubular metal eyelets secured through the wall of the laminate by clinching. These eyelets provide ventilation to the body encased in the cast.

It is an object of the present invention to provide an improved surgical cast venting device made with a stretchable piece of fabric material and at least one aeration device affixed to the inner surface of the material, this device being relatively inexpensive to manufacture and relatively easy to use.

It is a further object of the present invention to provide a surgical cast. venting device made with a stretchable piece of fabric material and having one or more aeration devices mounted on an inner surface of the fabric, this device being readily mountable and arranged on a body part, such as a broken limb, and capable of providing ventilation to the patient's skin area located within a surgical cast applied around the venting device.

SUMMARY OF THE INVENTION

According to one aspect of the invention, a surgical cast venting device includes a stretchable piece of porous fabric material having at least some elasticity and a flexible, tubular configuration and a substantial number of plastic tubular members. The piece of fabric has two opposite ends, which are open, and has an inner surface. The tubular members are distributed over, affixed to, and located on the inner surface of the piece of fabric. Each tubular member is open ended at both ends thereof. The venting device is adapted for placement around part of a human body or animal body prior to application of a surgical cast over this part of the body.

Preferably, the plastic tubular members are elongate and are adhesively bonded to the fabric material. These tubular members extend in a longitudinal direction relative to the fabric material, which has a length extending from one open end thereof to the opposite open end.

In a particularly preferred embodiment, the fabric material is stockinet.

According to another aspect of the invention, a surgical cast venting device includes a stretchable piece of fabric material having at least some elasticity, having two opposite ends and two opposite side edges, and having inner and outer surfaces. At least one aerating device is affixed to and located on the inner surface. Hook and loop type flexible fastener strips are affixed to the two opposite side edges and are arranged for detachable connection to one another in order to form the piece of fabric material into a tubular configuration or a portion of a tubular configuration. This venting device is adapted for placement around part of a human body or animal body prior to application of a surgical cast over this part of the body.

Preferably, the at least one aerating device is made of plastic and is adhesively bonded to the piece of fabric material.

According to a further aspect of the invention, a surgical cast venting device includes a stretchable piece of fabric material having at least some elasticity and a substantially tubular configuration. This piece has two opposite ends and an inner surface. The device further includes at least several, separate elongate plastic tubular members distributed over and affixed to the inner surface. These tubular members each are open ended at at least one end and have at least several ventilation holes formed in the tubular side thereof. These tubular members extend substantially from one of the opposite ends to the other of the opposite ends of the fabric material. This venting device is adapted for placement around part of a human body or animal body prior to application of a surgical cast over this part of the body.

Further features and advantages of the surgical cast venting device of the present invention will become apparent

DETAILED DESCRIPTION OF PREFERRED EMBODIMENT

Figure 1:
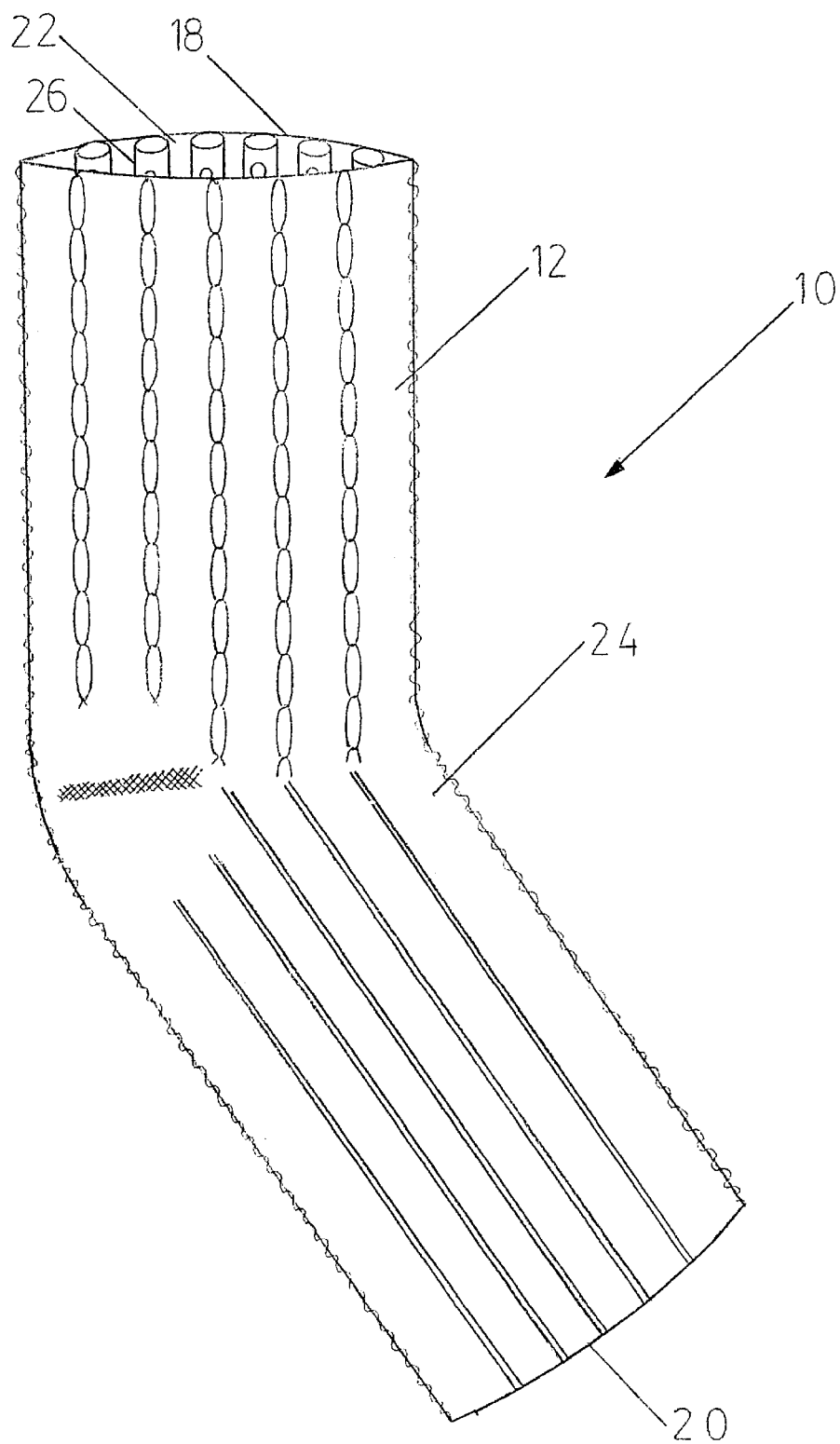
FIG. 1 is a side view of a surgical cast venting device constructed in accordance with the invention.
Figure 4:
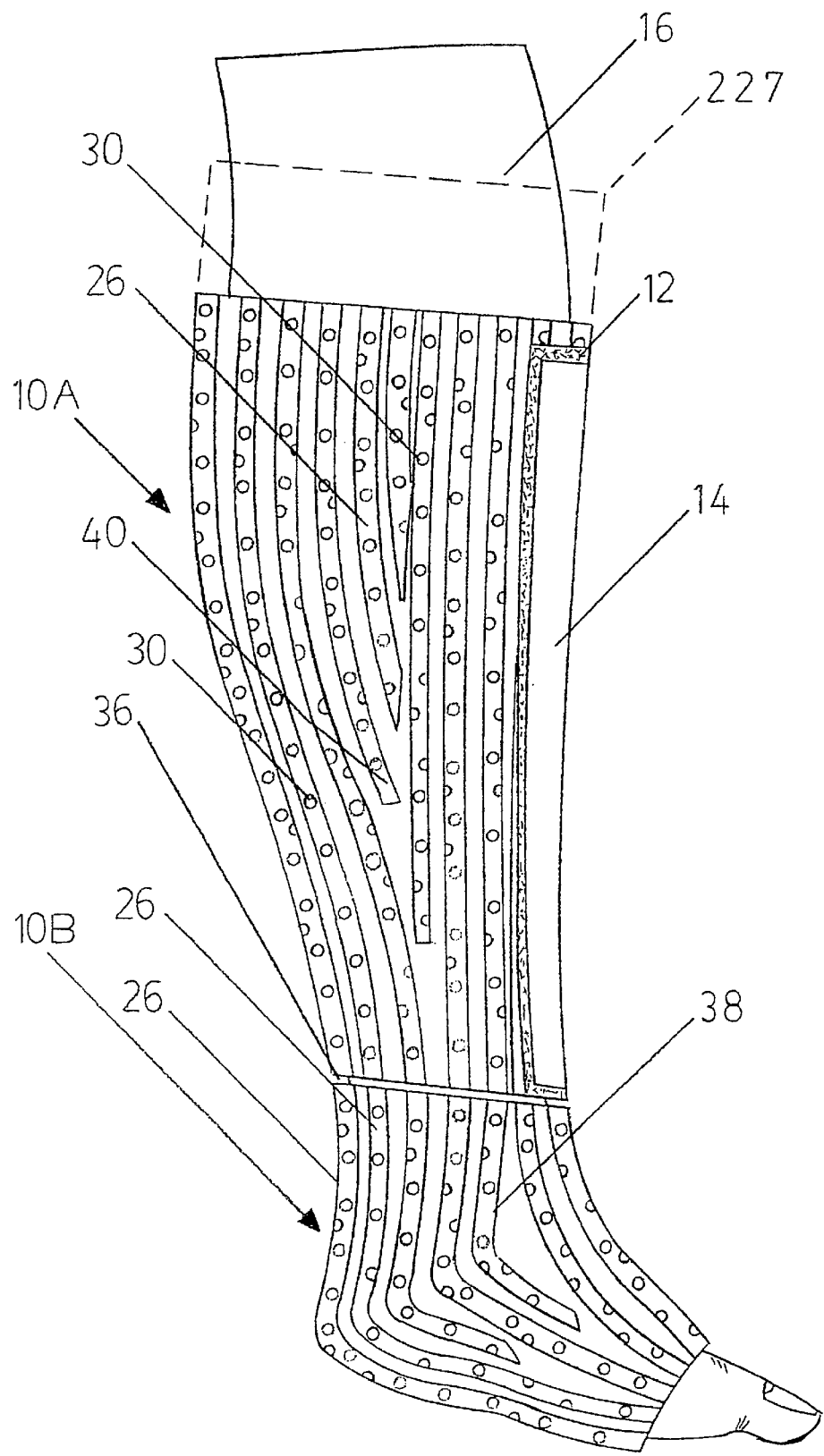
FIG. 4 is a side view showing two of the venting devices arranged over a patient's leg and foot with the stretchable fabric material mostly not shown in order illustrate the arrangement of the plastic tubular members.

A preferred form of surgical cast venting device 10 constructed in accordance with the invention is illustrated in FIG. 1. Although the illustrated venting device is shown with a substantial bend located centrally, the venting device can also be made straight for its entire length. The device 10 includes a stretchable piece of porous fabric material 12 having at least some elasticity and preferably a significant amount of elasticity in order to permit the device to be slid over and positioned on a person's or animal's limb that has been broken. It will be understood that the venting device of the invention is adapted for placement around a part of a human body or animal body prior to application of a surgical cast over this part of the body. The surgical cast itself can be of standard construction and made of plaster of paris, for example. A portion of a surgical cast 14 is shown in FIG. 4. The venting device 10 shown in FIG. 1 has a flexible, tubular configuration and it is generally suitable for arrangement around an arm or a person's leg 16 as shown in FIG. 4. The venting device has two opposite ends at 18 and 20, which are open and has an inner surface 22, the nature of which is illustrated in FIG. 2, and an outer surface 24.

Arranged on the inner surface of the preferred venting device are a substantial number of plastic tubular members 26 which are distributed over and affixed to the inner surface. Preferably, each of these tubular members 26 is open-ended at both ends thereof, including the end 28 illustrated in FIG. 2. For some applications of the venting device and depending also on the nature of the plastic tubular member itself, the tubular member could be constructed with only one open end while still providing adequate ventilation under the cast.

Figure 2:
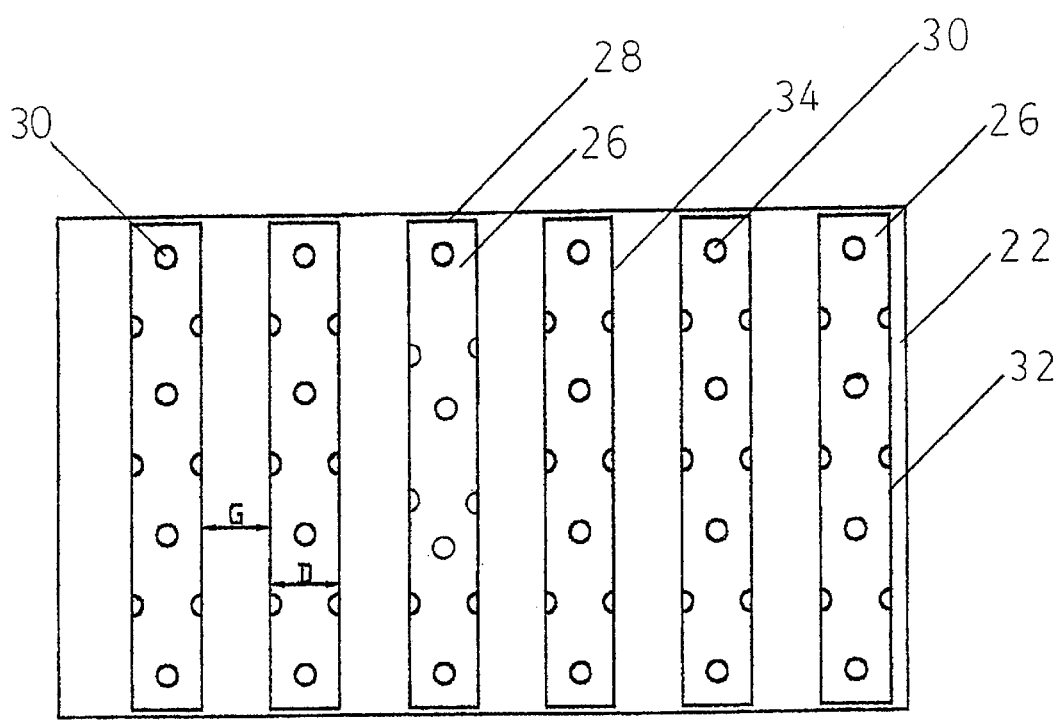
FIG. 2 is a detail view showing a portion of the inner surface of the venting device of FIG. 1, this portion being shown flat for ease of illustration.

Preferably the plastic tubular members 26 are elongate as illustrated in FIGS. 2 and 4 and are adhesively bonded to the fabric material 12. The preferred adhesive is any suitable known type of medical adhesive that is non-toxic and that will bond to both the flexible plastic from which the tubular members are made and the fabric material which can be made of cotton or from synthetic threads such as nylon and polyester. In the preferred venting device illustrated in FIGS. 1, 2 and 4, the tubular members 26 extend in a longitudinal direction relative to the fabric material 12, which has a length extending from the open end 18 to the open end 20. Each plastic tubular member 26 has at least several ventilation holes, and preferably a substantial number of ventilation holes 30 formed in the tubular side thereof and distributed along the length thereof. These holes can be round as shown and quite small, for example ¹⁄₁₆th inch or less. There should be holes on the side of the tubular member opposite the fabric material and also on the two rounded sides indicated at 32 and 34 in FIG. 2 that are located at 90 degrees approximately to the aforementioned side. This arrangement enables air to pass freely into and out of the tubular members which preferably have a diameter of less than ½ inch and more preferably no more than ¼ inch.

Preferably, the plastic from which the tubular members are made is a medical grade plastic and is selected so as to be as compatible with the skin as possible and non allergenic. The plastic must also be sufficiently flexible to mold itself to the contour of the limb when the venting device is applied, particularly when the exterior cast material is being or has been applied about the venting device.

Preferably, at least a majority of the plastic tubular members extend substantially the length of the fabric material as illustrated in FIG. 4 where there are two venting devices with the tubular venting device 10A extending over the calf of the person's leg and a second venting device 10B extending over the ankle region and a major portion of his foot. These two venting devices meet at the annular joint 36. If the venting device has been specially made to fit a particular area of the body, some of the tubular members such as those indicated at 38 and 40 in FIG. 4 may not extend the entire length of the venting device but only, for instance, about one half of the length. Using these shorter tubular members, the venting device can be contoured to fit a particular shape while still maintaining about the same spacing or gap between adjacent tubular members. Preferably each plastic tubular member is located close to but spaced apart from adjacent ones of the plastic tubular members as illustrated in FIGS. 2 and 4. For example, the gap G indicated in FIG. 2 which may be substantially uniform can be approximately equal to the diameter D of the adjacent tubular members. A smaller relative gap is also possible but the gap should be sufficient to allow adequate air flow in the longitudinal direction between the tubular members. Also, the gap G should not be too large in order that the tubular members can act as proper spacers to maintain the rigid cast material away from the adjacent skin area. In other words, the gap should not be so large that when the cast is applied, there is in effect no air gap in some locations between the skin and the rigid cast layer.

A preferred form of the fabric material is known as stockinet which is a commonly available, machine-knitted cotton fabric with some elasticity, a type of material commonly used in the making of undergarments. However, instead of a natural fiber such as cotton, the fabric layer can also be made from synthetic fibers for purposes of the present invention, for example, nylon, rayon and polyester. It should be noted that it is also possible to apply a layer of stockinet directly over the body part over which the venting device of the present invention is being placed, in order to avoid contact between the plastic tubular members used on the venting device and the patient's skin. The preferred material for this stockinet material is natural cotton because of its absorbent qualities.

Figure 3:
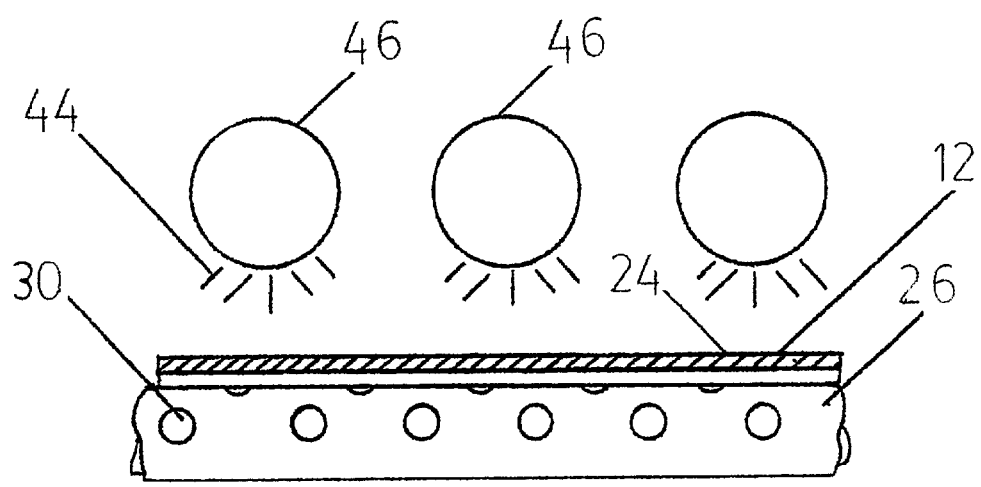
FIG. 3 is a detail edge view of a portion of a venting device illustrating the manner in which the tubular members are adhered to the porous fabric.

FIG. 3 illustrates a preferred method for attaching the plastic tubular members to the fabric material. The individual tubular members 26 can be placed in a suitable holder of the required tubular or cylindrical shape so that they can be held in their correct relative positions for the bonding process. With the tubular members in their correct relative position, the fabric layer material 12 is placed over the holder and the tubular members and then a suitable medical adhesive is applied to the outer surface 24 of the fabric along attachment areas directly opposite the tubular members. Because of the porous nature of the fabric material, the adhesive soaks through the fabric to the tubular members at which point the adhesive is cured by exposure to ultraviolet light indicated schematically at 44 which can be created by ultraviolet light bulbs or tubes 46 which can be arranged about the exterior of the tubular fabric material.

Figure 5:
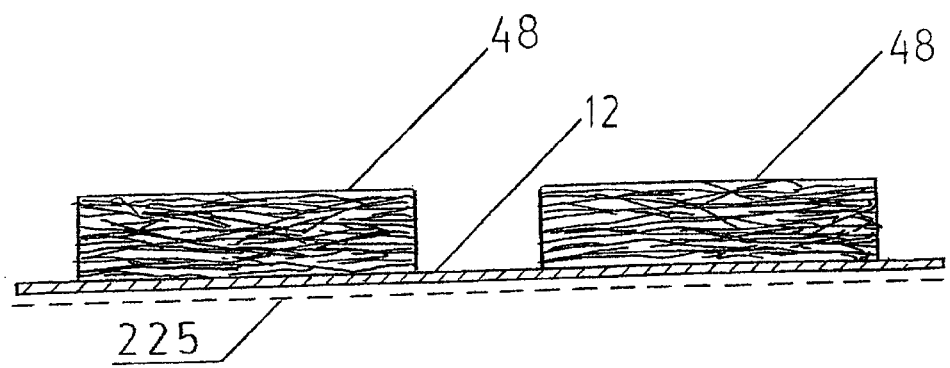
FIG. 5 is a detail edge view showing a portion of another embodiment of the venting device, this embodiment showing aerating devices in the form of a layer of non-woven, plastic threads.
Figure 6:
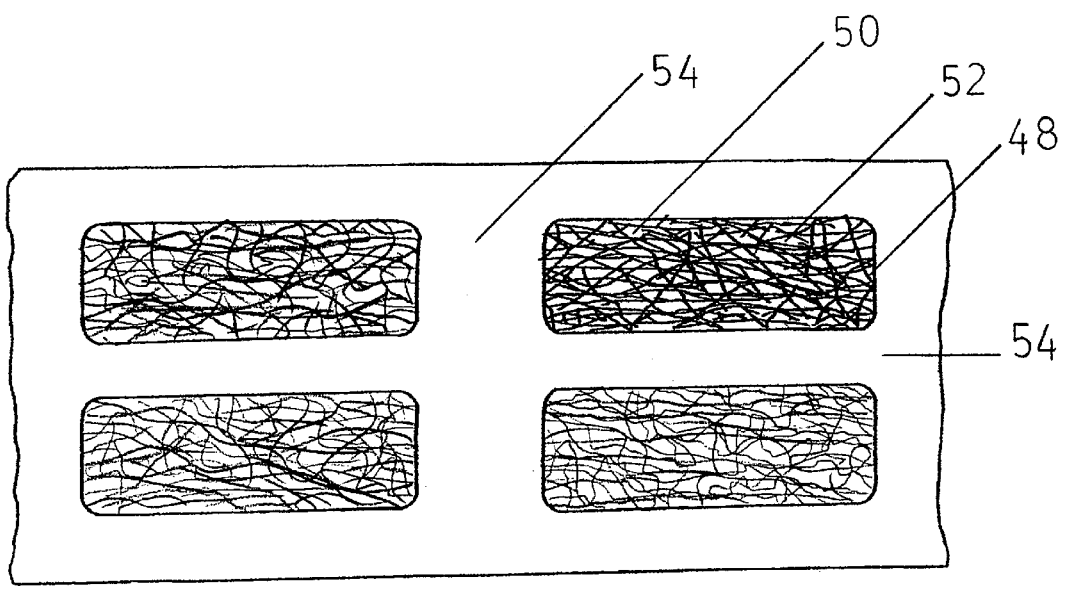
FIG. 6 is a top view of the small section of the venting device shown in FIG. 5.

The plastic aerating devices that are affixed to the inner surface of the venting device can take various forms other than the described elongate tubular members. One alternate form of aerating device is illustrated in FIGS. 5 and 6. These aerating devices are flexible layers 48 of interconnected, non-woven plastic threads or strips 50. Each layer 48 has numerous small air passageways indicated at 52 that are formed therein. The thickness of each layer can be only ¼ inch or less and the layers can be separated by longitudinally and transversely extending air gaps 54. The layers are again adhesively bonded to a piece or tube of fabric material 12 and it will be understood that in the case of a tubular piece of fabric material, the layers 48 are arranged on the interior surface of the material. The layers 48 can have a consistency or make-up similar to natural "loofah", commonly used as a body sponge or body cleaning product. However, the layers 48 are made sufficiently thin and they are provided with sufficiently large air spaces between the plastic threads that each layer is flexible and is able to bend to the body contour.

Although the illustrated layers are rectangular in shape, clearly other shapes are also possible, including square, triangular and elongate strips. Also, the size of each layer and the size and number of air gaps between the layers can vary depending upon the flexibility of each layer and the proposed use for the particular venting device. The overall criteria for the venting device using such layers is that the venting device must have sufficient elasticity in order to permit it to expand and to be pulled over the body part and the arrangement of the layers must be sufficiently flexible to permit the venting device to adjust itself closely to the contour of the body part prior to application of the cast material.

Figure 7:
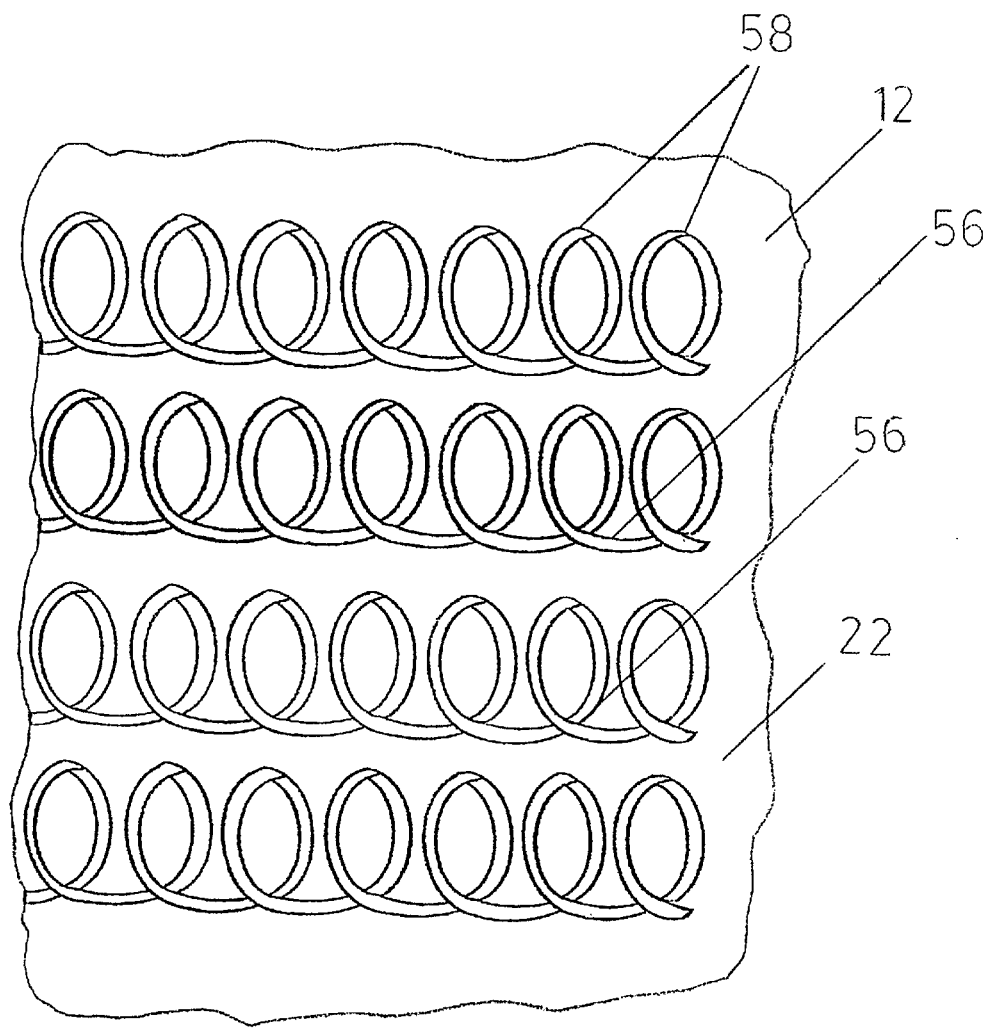
FIG. 7 is a plan view similar to FIG. 6 but showing a further embodiment of a venting device in accordance with the invention.

Another form of aerating device is illustrated in FIG. 7 which shows only a portion of the interior surface of a venting device formed with fabric material 12 on its exterior. In this case, the aerating devices comprise a substantial number of spiral-shaped, resilient plastic members 56 which are distributed over the inner surface 22 of the venting device. The spiral shaped members 56 can extend in a longitudinal direction of the venting device, that is from one open end to the opposite open end. Again, each of the plastic members 56 is close to but spaced apart from adjacent ones of the plastic members 56.

The spiral-shaped members 56 preferably have a maximum exterior diameter less than one half inch and more preferably no more than ¼ inch. The plastic thread or wire from which each member 56 is formed should have sufficient diameter or thickness that it will not irritate or cut a patient's skin when the venting device is put in place. Furthermore, adjacent individual spirals 58 should be reasonably closely spaced, again so that they will not irritate or cut into the patient's skin, which may be sensitive, and also so that the member 56 can adequately support the surrounding rigid cast without collapsing under the applied force.

Figure 8:
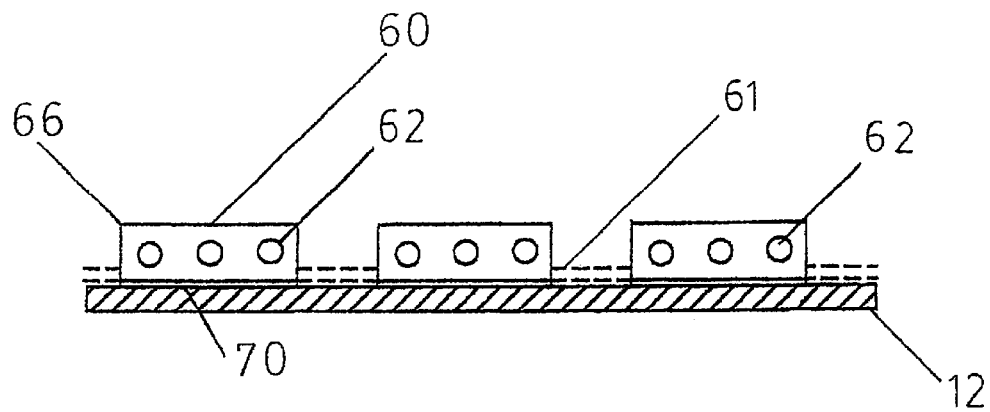
FIG. 8 is a detail edge view of a section of still another embodiment of the venting device, this version employing plastic ring members.
Figure 9:
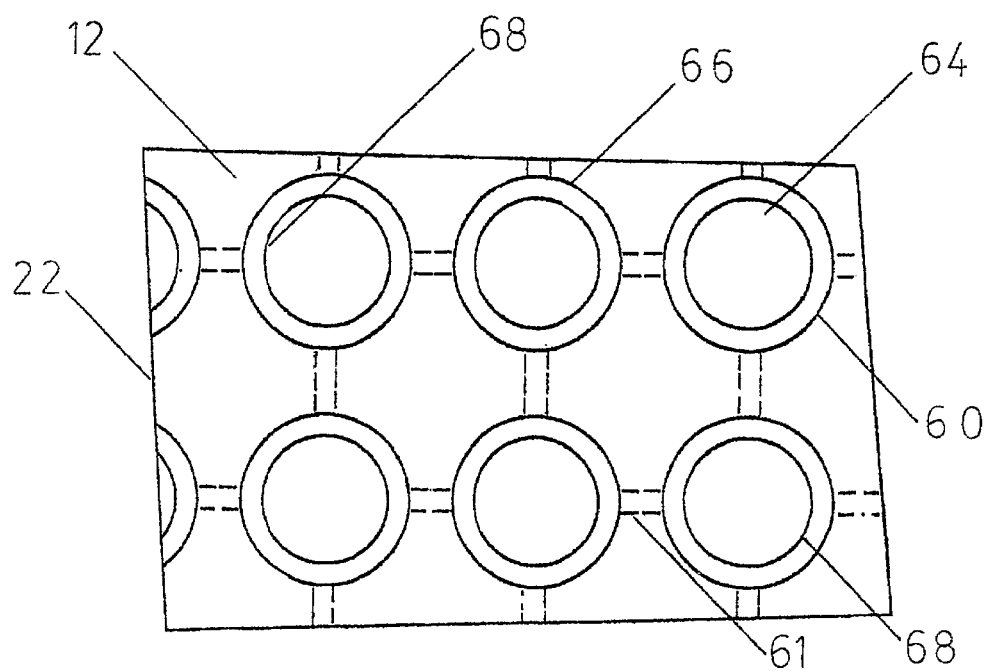
FIG. 9 is a plan view of the section of the venting device shown in FIG. 8.

Turning now to a further embodiment of a venting device according to this invention, this embodiment being illustrated in FIGS. 8 and 9, the plastic members which are affixed to the piece of fabric material 12 of the venting device are in the form of ring-like plastic members 60, each of which is perforated with a number of small holes 62 about its perimeter. These holes permit the passage of air to and from the circular space 64 located inside each ring-like member. The plastic members 60 are distributed evenly or substantially uniformly over the inner surface 22 of the piece or tube of fabric material. The size of the member 60 can vary and will depend to some extent on the particular use to which the venting device is to be put. Typically, the preferred exterior diameter of each ring-like member 60 is no more than one inch and more preferably is no more than one half inch. The thickness or depth of each ring-like member can also vary but preferably is no more than ¼ inch. The outer, annular edges of each member 60, these edges being indicated at 66, can be rounded, if desired, to avoid unnecessary irritation of the user's skin and to make the wearing of the venting device as comfortable as possible. The annular interior edges 68 can also be rounded, if desired. Again, it will be understood that the members 60 are preferably bonded by a suitable medical adhesive indicated at 70. If desired, the ring-like members 60 can be attached to the fabric material in a manner similar to the elongate tubular members described in conjunction with FIG. 3 of the drawings.

Optionally, the ring like members 60 can be interconnected by integral, plastic web connectors 61 illustrated in dash lines in FIGS. 8 and 9. These web connectors can interconnect adjacent members 60 in order to maintain the uniform spacing of the members 60, particularly before these members are bonded to the fabric material. The plastic connectors 61 can help support the ring-like members 60 even after the latter have been bonded to the fabric material and help to prevent the ring-like members from becoming detached or from becoming displaced from their desired position. If desired, these thin plastic connectors can be broken in order to provide the venting device with sufficient flexibility and elasticity when it is being applied to the body part.

Figure 10:
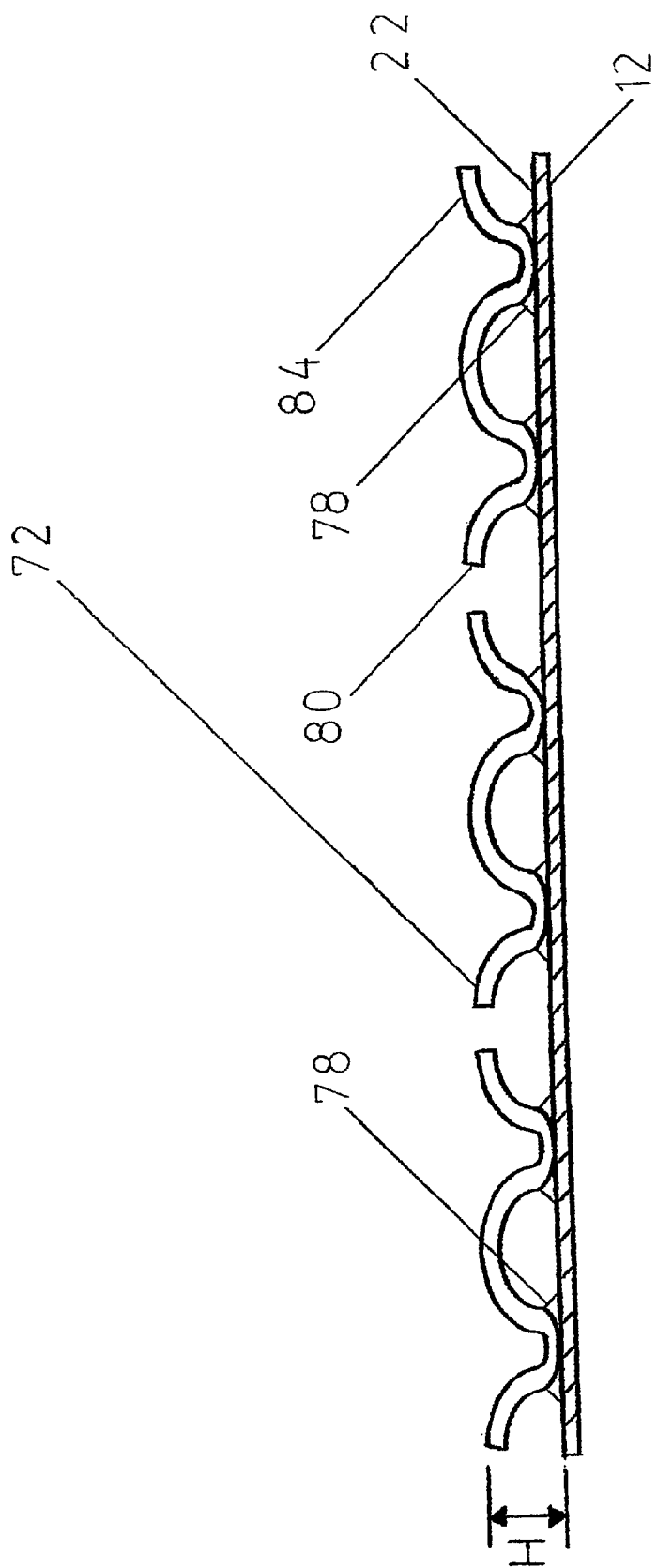
FIG. 10 is an edge view of a small section of a further embodiment of the venting device, this version employing corrugated plastic members.
Figure 11:
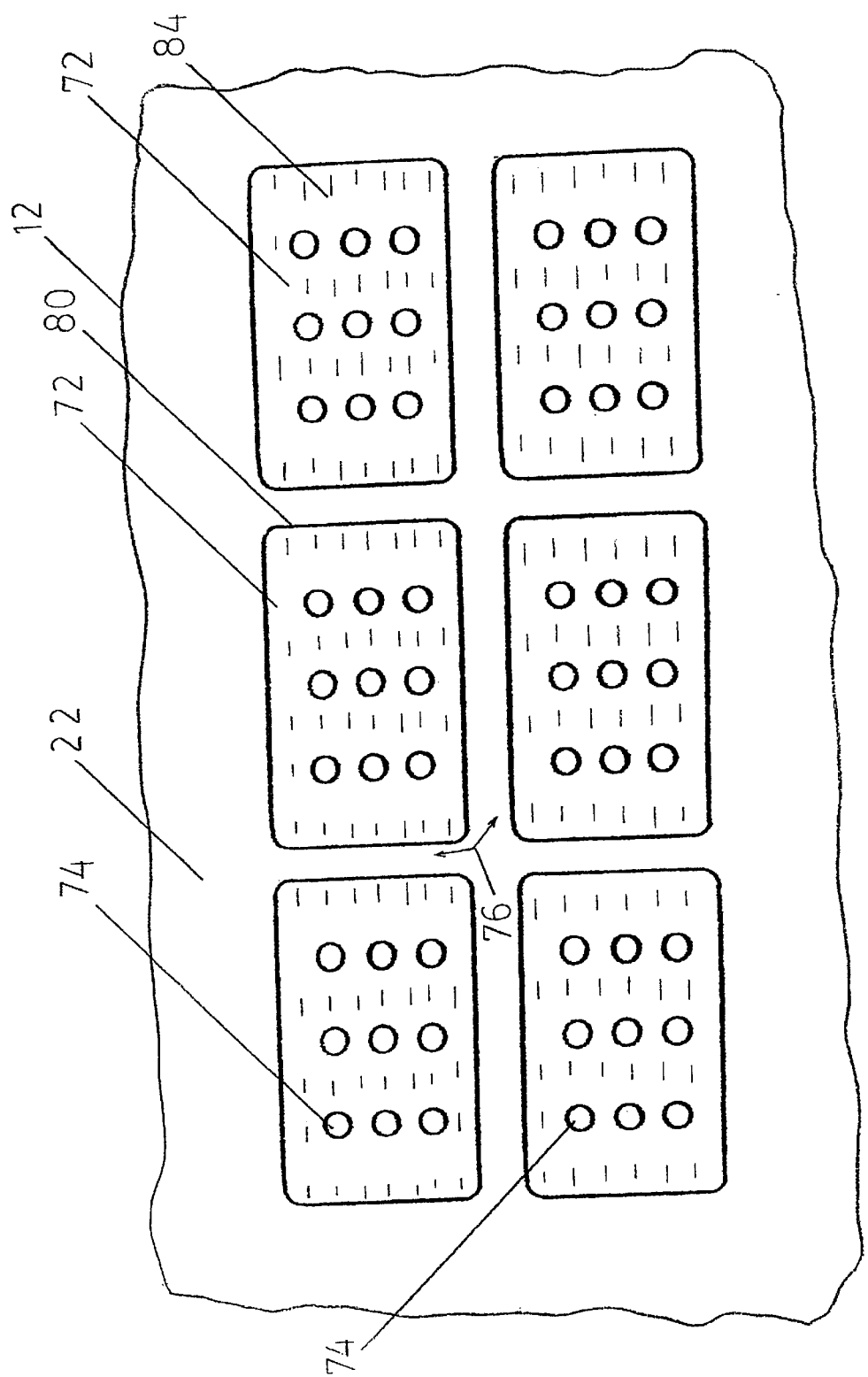
FIG. 11 is a plan view of the small section of the venting device shown in FIG. 10.

FIGS. 10 and 11 illustrate yet another version of the venting device of the invention, this version using aerating devices, that are affixed to the inner surface 22 of the fabric material, in the form of at least several and preferably a substantial number of corrugated plastic members 72, each of which is perforated with a substantial number of small holes 74 which can be circular. The size of these holes can be as small as ¹⁄₁₆th inch or less in diameter and these holes tend to increase the circulation of air about the corrugated members. The members 72 are distributed preferably uniformly over the inner surface 22 of the fabric material 12. The members 72 are preferably separated by longitudinally and transversely extending air gaps 76, the width of which can vary but preferably these gaps should be sufficiently wide to allow adequate air flow between the corrugated members and they should not be so wide as to allow contact between the rigid cast material and the patient's skin. Preferably the width of the gap 76 is less than ½ inch while the preferred height H of each corrugated member 72 is no more than ¼ inch. Again, the members 72 are preferably affixed by a suitable medical adhesive indicated at 78. Preferably the opposite edges 80 and 82 are rounded to avoid irritation to adjacent skin and the edge region 84 forming each of the edges 80 and 82 should not extend towards the skin but should either extend parallel to the adjacent skin as shown or extend away from the skin. Although only a couple of corrugations are shown on the illustrated plastic member 72, it will be appreciated that these members could have more corrugations such as four or five or more, particularly if the corrugations are made quite small in width.

Figure 12:
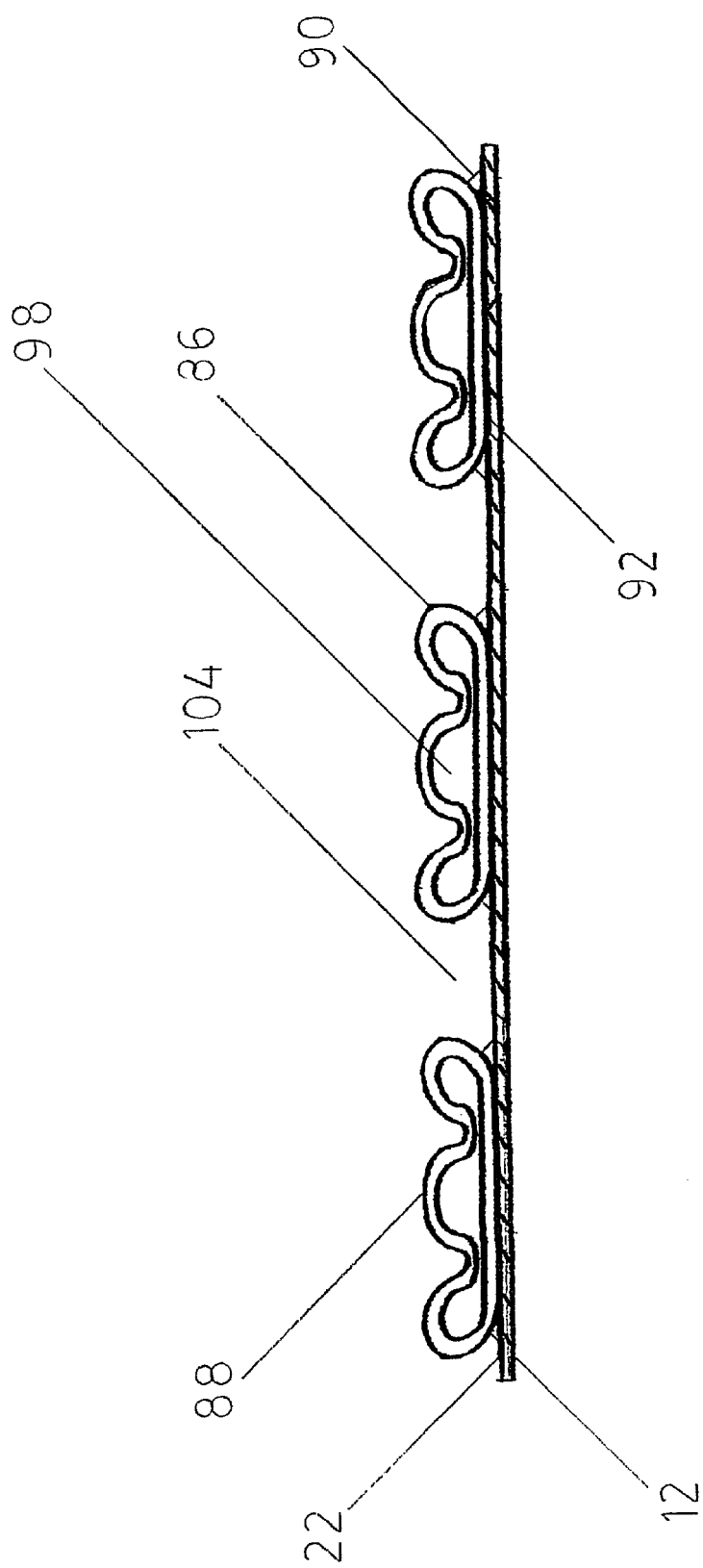
FIG. 12 is an edge view of still another embodiment of the venting device, this version employing plastic members with corrugated tops.
Figure 13:
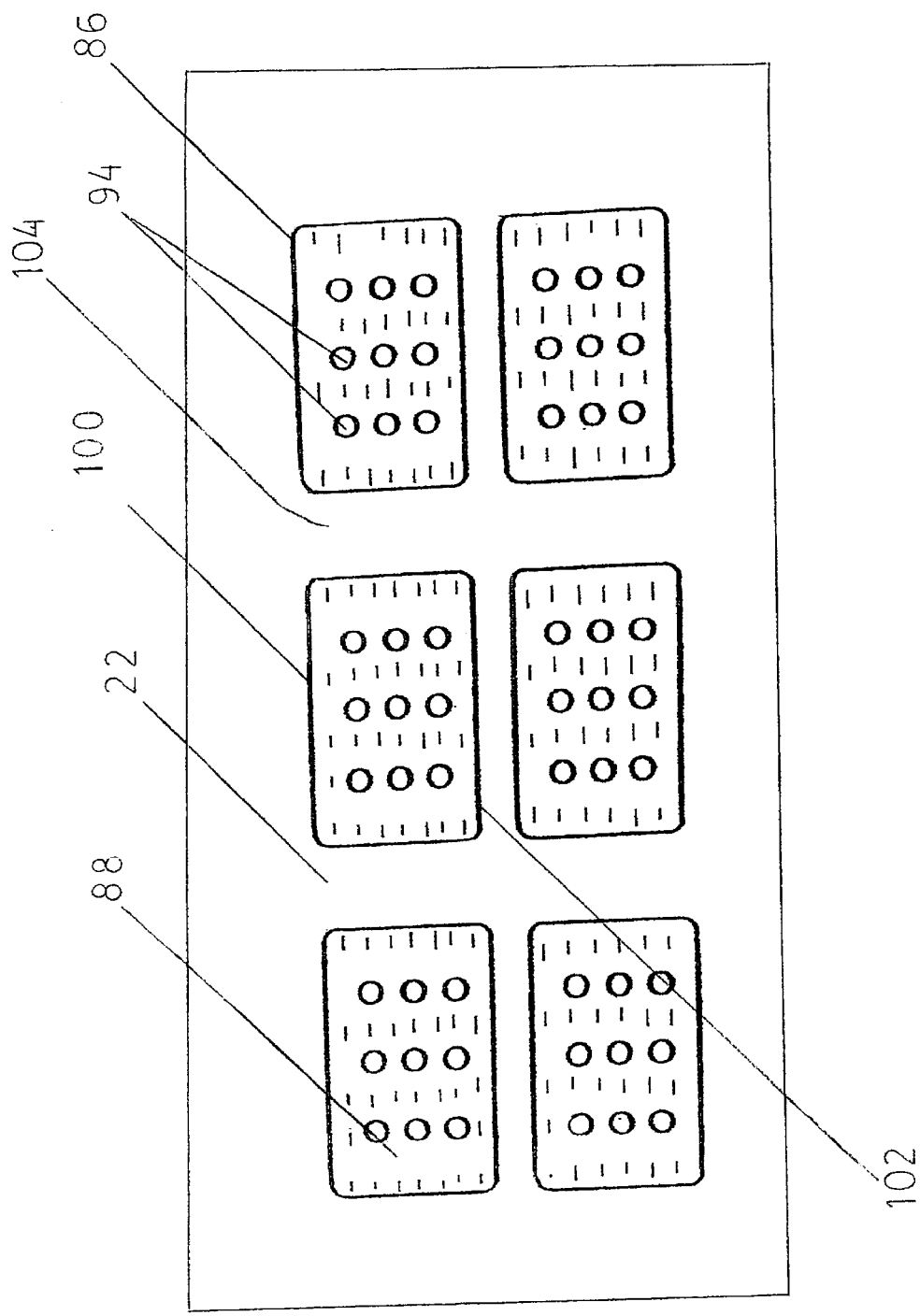
FIG. 13 is a plan view of the small section of the venting device shown in FIG. 12.

Still another type of aerating device for the venting device of the invention is illustrated in FIGS. 12 and 13. These aerating devices which are affixed to the inner surface 22 are also corrugated plastic members but these members 86 have corrugated top sections 88 and planar bottoms 90 integrally connected to the top sections. The bottoms 90 are affixed by means of a suitable adhesive 92 to the porous fabric material 12. The top sections 88 are perforated with a substantial number of small holes 94 which can be round. These holes open into an air space 98 formed between each top section and its respective bottom 90. It will be understood that each corrugated member 86 is preferably open-ended at 100 and 102.

Again, the corrugated members 86 are spaced apart by longitudinally and transversely extending air gaps 104 which are sufficiently wide to permit the free flow of air between the members 86 and which are not so wide as to allow contact between the surrounding rigid cast and the patient's skin. Preferably the maximum width of the air gaps 104 is less than ½ inch. The dimensions and height of each corrugated member 86 can be similar to the corrugated members illustrated in FIGS. 10 and 11.

Figure 14:
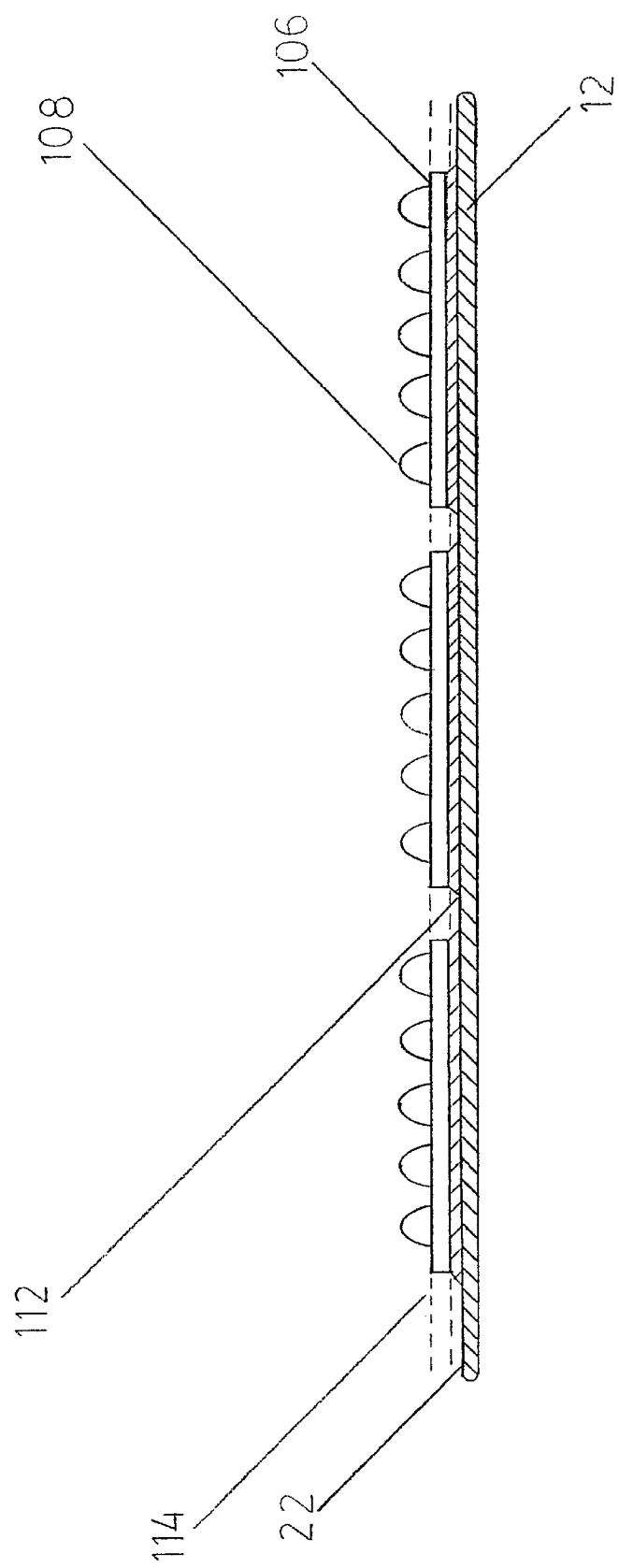
FIG. 14 is an edge view of still another embodiment of the venting device, this version employing a grid of plastic members with a number of bumps formed on their top surfaces.
Figure 15:
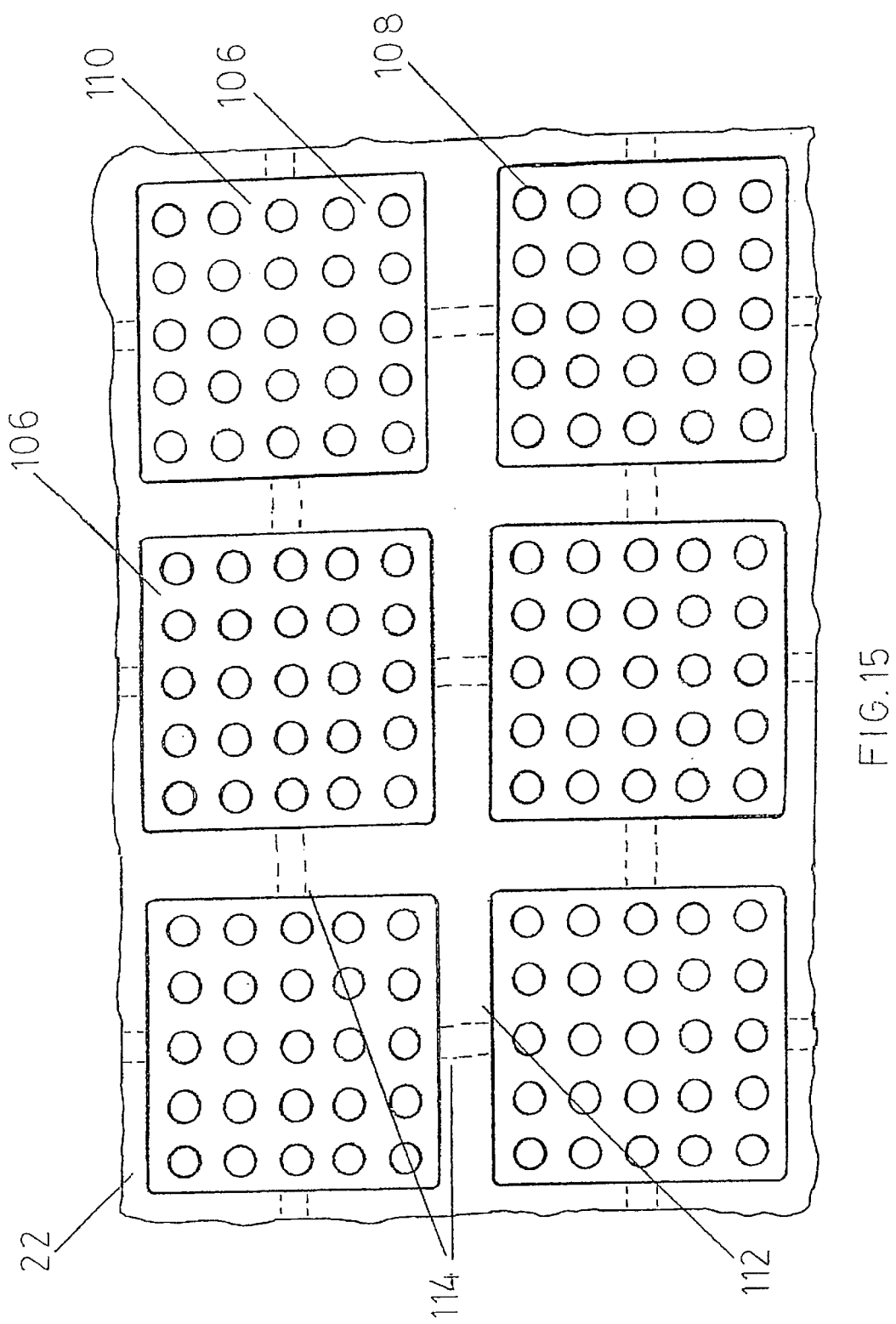
FIG. 15 is a plan view of the section of the venting device shown in FIG. 14.

Yet another form of aerating device for a venting device 10 of the invention is illustrated in FIGS. 14 and 15. In this embodiment, the aerating devices affix to the inside surface 22 of the venting device comprise at least several and preferably a substantial number of plastic members 106 with at least several and preferably a substantial number of bumps or protrubences 108 formed on an outer surface 110 of the plastic member. The bumps, which are preferably rounded as shown, project away from the inner surface 22 of the piece of fabric material. The plastic members, which can have a square shape as shown, are preferably distributed evenly over the inner surface 22 and are spaced apart from one another. Preferably there are longitudinally and transversely extending air gaps 112 extending between the plastic members 106. These air gaps can be similar in width to the air gaps 76 and 104 of the embodiments illustrated in FIGS. 10 to 13. Although the illustrated members 106 have a generally square shape, it will be appreciated that they can also have a rectangular, triangular, or rounded shape. Also, although the members 106 are illustrated with twenty-five bumps 108 laid out in a regular grid on the outer surface, the number of bumps can be fewer or more than the number of bumps shown.

Optionally, the plastic members 106 can be interconnected by means of thin, plastic connecting members 114 which can be readily broken, if required. The connectors 114 can be formed integrally with the plastic members 106 in the same molding process. By using the connectors 114, the numerous plastic members 106 will be correctly spaced and oriented prior to bonding and as they are bonded by adhesive to the fabric material 12. Again, after the members 106 have been bonded to the fabric material, the thin plastic connectors 114 can be readily broken, as required, to provide the venting device with the desired expandability and flexibility for mounting on a body part.

Figure 16:
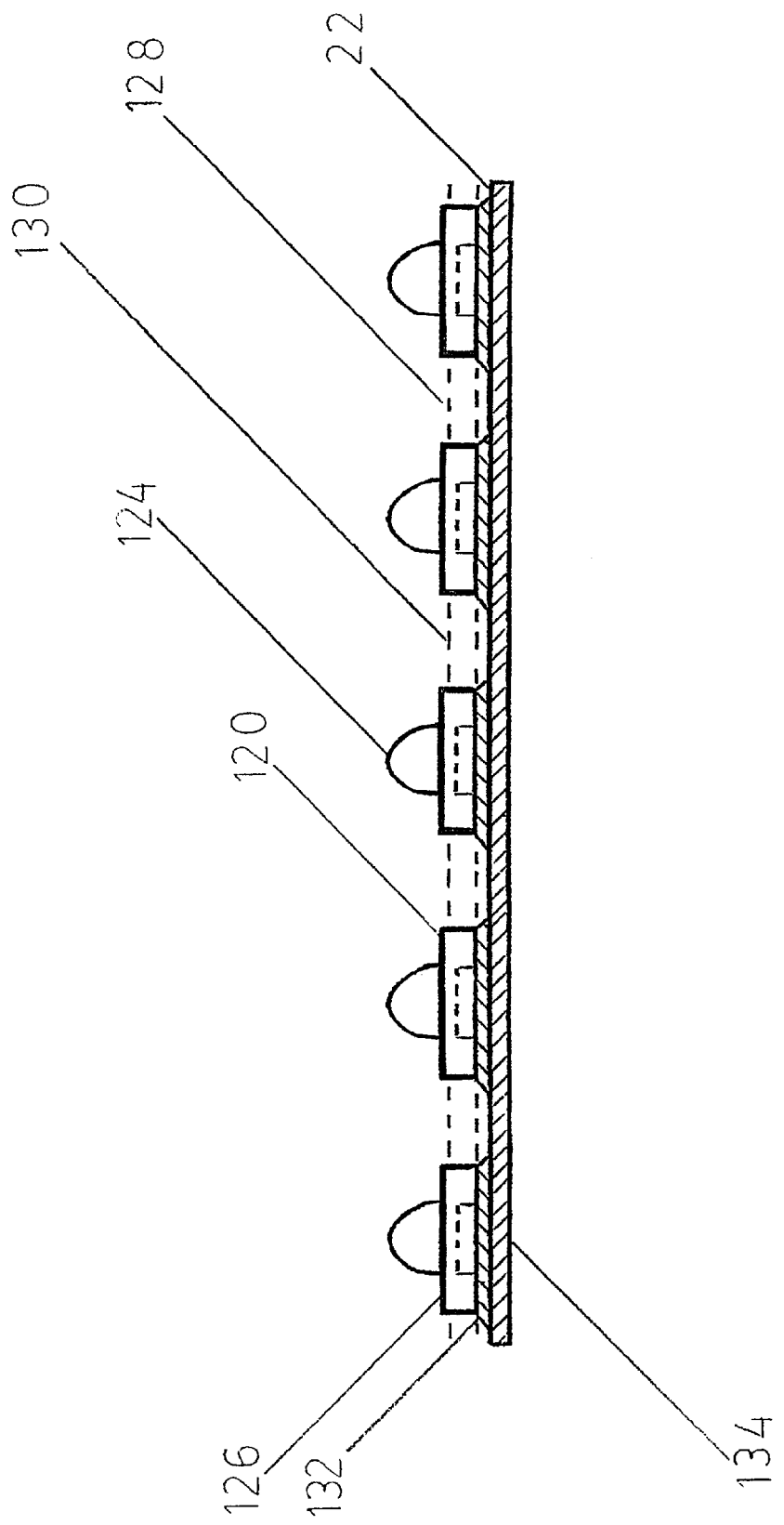
FIG. 16 is an edge view of another venting device of the invention, this embodiment employing a grid work of small plastic members having a bump formed in each of their top surfaces.
Figure 17:
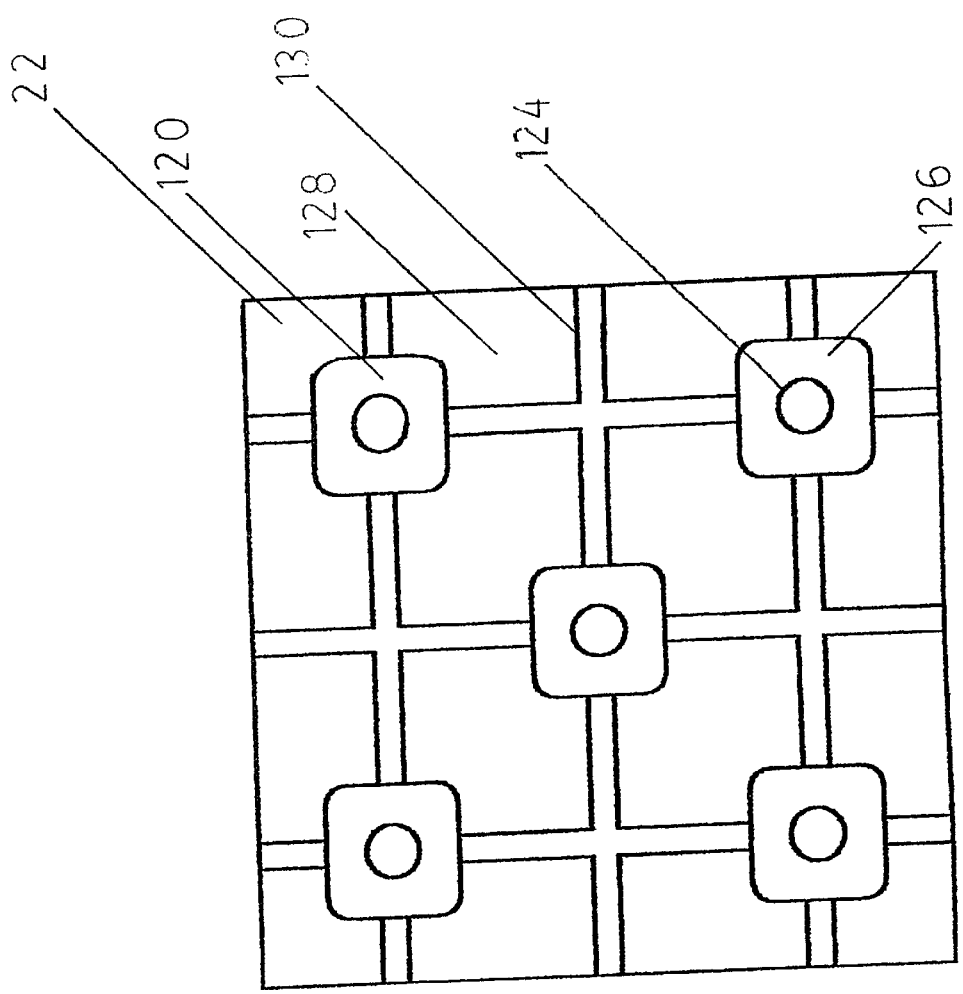
FIG. 17 is a detail plan view of the section shown in FIG. 16.

Yet another form of aerating device for use in the venting device of the invention is illustrated in FIGS. 16 and 17. In this version, the plastic aerating devices fixed to the inner surface 22 of the venting device are at least several and preferably a substantial number of plastic members 120 which can be quite small and relatively closely spaced. Unlike the members shown in FIGS. 14 and 15, each of the members 120 is formed with a single bump or protuberance 124 which is preferably rounded and centrally located on the outer surface 126 of the member. The single bump projects away from the inner surface 22 of the fabric material. The plastic members 120 are uniformly distributed over the inner surface 22 and are spaced apart from one another by longitudinally and transversely extending air gaps 128.

As in the previous embodiment, the small plastic members 120 can optionally be interconnected by means of integral connecting plastic webs or links 130 shown in dash lines in FIG. 16 but in solid lines in FIG. 17. Again, these connecting webs help to maintain the spacing between the plastic members 120 and to maintain their orientation before they are bonded to the fabric material by adhesive. This adhesive is indicated at 132 and, as in the first embodiment, this adhesive is applied to the outer surface 134 and it then soaks through the fabric material to the adjacent surface of the plastic member 120 before being cured and drying. Again, the small connecting web members 130 can readily be broken to give the venting device adequate flexibility and expandability.

Figure 18:
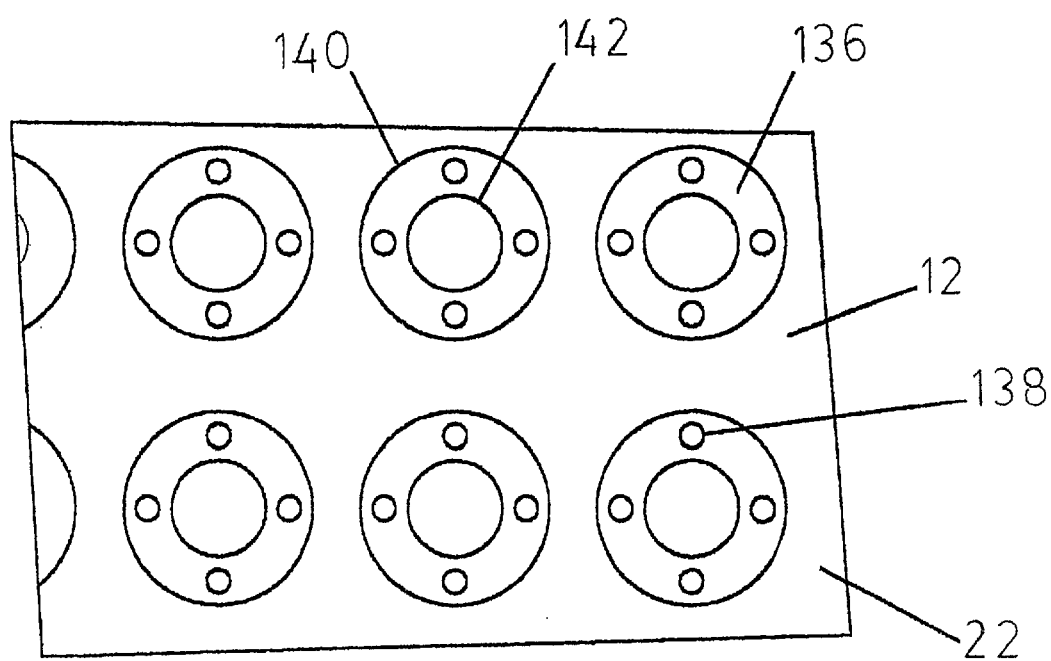
FIG. 18 is a detail plan view of the inner surface of a further embodiment of the venting device.

Another version of an aerating device is illustrated in FIG. 18 wherein the aerating devices affixed to the inner surface 22 comprise a substantial number of ring-like plastic members 136 which are perforated with small holes 138. Although only four holes 138 are shown in each member 136 in FIG. 18 for ease of illustration, it will be appreciated that the members 136 can have more small holes such as eight, twelve or more. The provision of the holes 138 helps to reduce the area of the fabric material that is actually covered by the plastic of the ring members. The annular inner and outer edges 140 of each ring-like member can be rounded to help lessen skin irritation by these members. The size of these members 136 can be approximately the same size as the ring-like members 60 illustrated in FIGS. 8 and 9. Also, instead of being round members as illustrated, the members 136 could instead be oval-shaped or even square or rectangular in shape.

Figure 19:
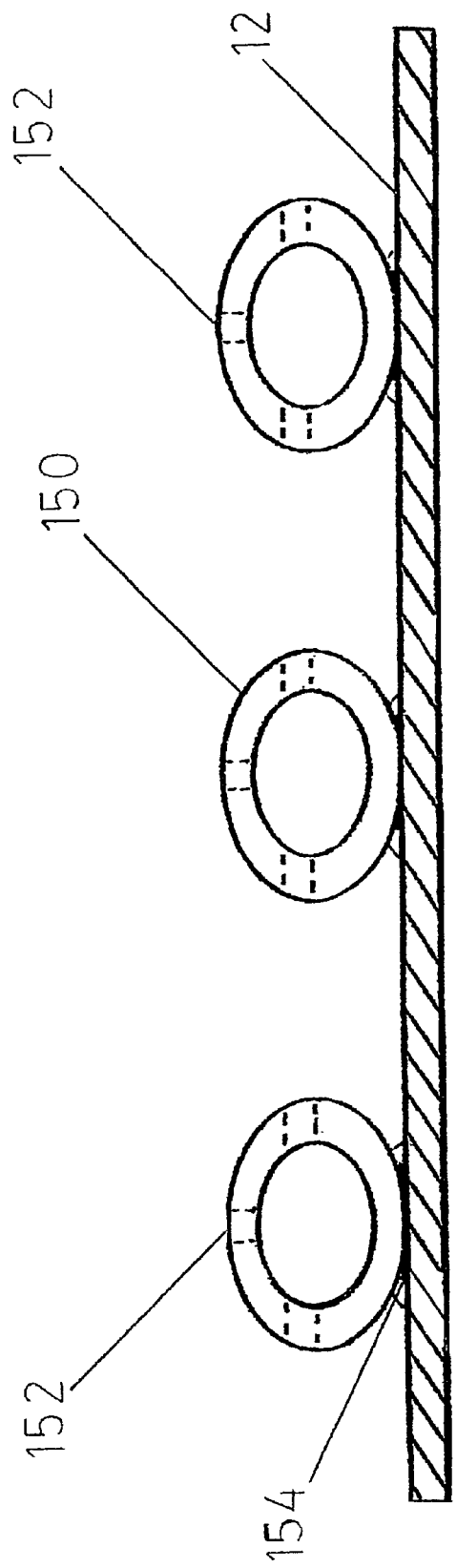
FIG. 19 is an edge view illustrating plastic tubular members having an oval cross-section, such members being usable in still another version of the invention.

Another form of aerating device similar to the first described version is illustrated in FIG. 19. In this version, there are again elongate tubular members but these plastic members 150 are somewhat flattened rather than being round in cross-section. In other words, these members 150 have an oval-shaped cross-section and because they can then be larger in size, they can have more small holes 152 formed in their sides. Otherwise the construction of this version of the venting device is substantially the same as the first described version illustrated in FIGS. 2 and 4. Again, the plastic members 150 extend parallel to one another and are spaced apart generally a uniform distance. They are affixed by a suitable medical adhesive indicated at 154 to the fabric material 12.

Figure 20:
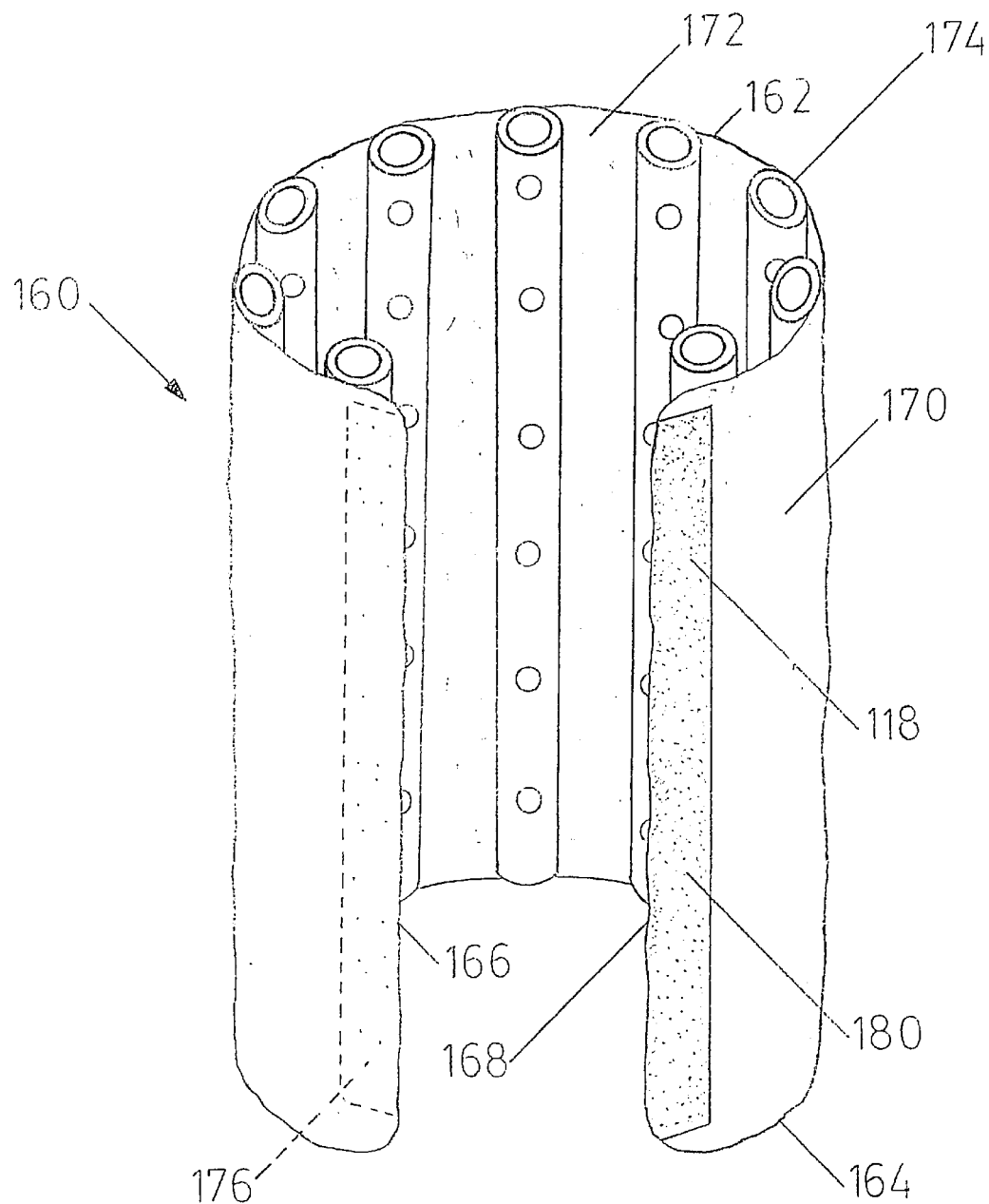
FIG. 20 is a perspective view taken from a front side showing another version of the venting device, this version employing a stretchable piece of fabric material provided with hook and loop type flexible fastener strips affixed to two opposite side edges.

Another form of surgical cast venting device of the invention is illustrated in FIG. 20 of the drawings. This version indicated generally at 160 includes a stretchable piece of fabric material having at least some elasticity and this stretchable piece has two opposite ends 162 and 168 and two opposite side edges 166 and 168. The stretchable piece also has an outer surface 170 and an inner surface 172. Again, aerating devices, preferably in the form of elongate plastic tubes 174 are affixed to and located on the inner surface 172 and can extend from the one end 162 to the opposite end 164.

Hook and loop type flexible fastener strips 176 and 178 are affixed to the two opposite side edges of this venting device and arranged for detachable connection to one another in order to form the piece of fabric material into a tubular configuration similar to the tubular configuration of the first embodiment. Alternatively, the venting device 160 can be detachably connected by means of the fastener strips to one or more similar venting devices to form a larger, tubular venting device, for example, one that can be applied around a patient's stomach region or chest region. In any event, it will be understood that this venting device is adapted for placement around part of the human body or animal body prior to application of a surgical cast over this part of the body. The fastener strips 176, 178 can be of standard construction and can be the type sold under the trademark or trade name Velcro. Thus, one of the strips, preferably the strip 178 on the outer surface of the fabric material, is covered with numerous small hook members 180 while the other strip, preferably the inside strip 176 outlined in dash lines in FIG. 20, is covered with numerous small loops made from strong threads or threadlike material. The fastener strips can be affixed in any suitable manner to the fabric material which is preferably stockinet. A preferred form of attachment for each of the fastener strips is a suitable, known form of medical adhesive but stitching can also be used to attach these strips.

As in the previously described venting devices, in the venting device 160 of FIG. 20, the aerating devices are tubular members 174 that are adhesively bonded to the fabric material on one side thereof. These aerating devices 174 cover at least a major portion of the inner surface in a substantially uniform manner in the preferred embodiment.

Figure 21:
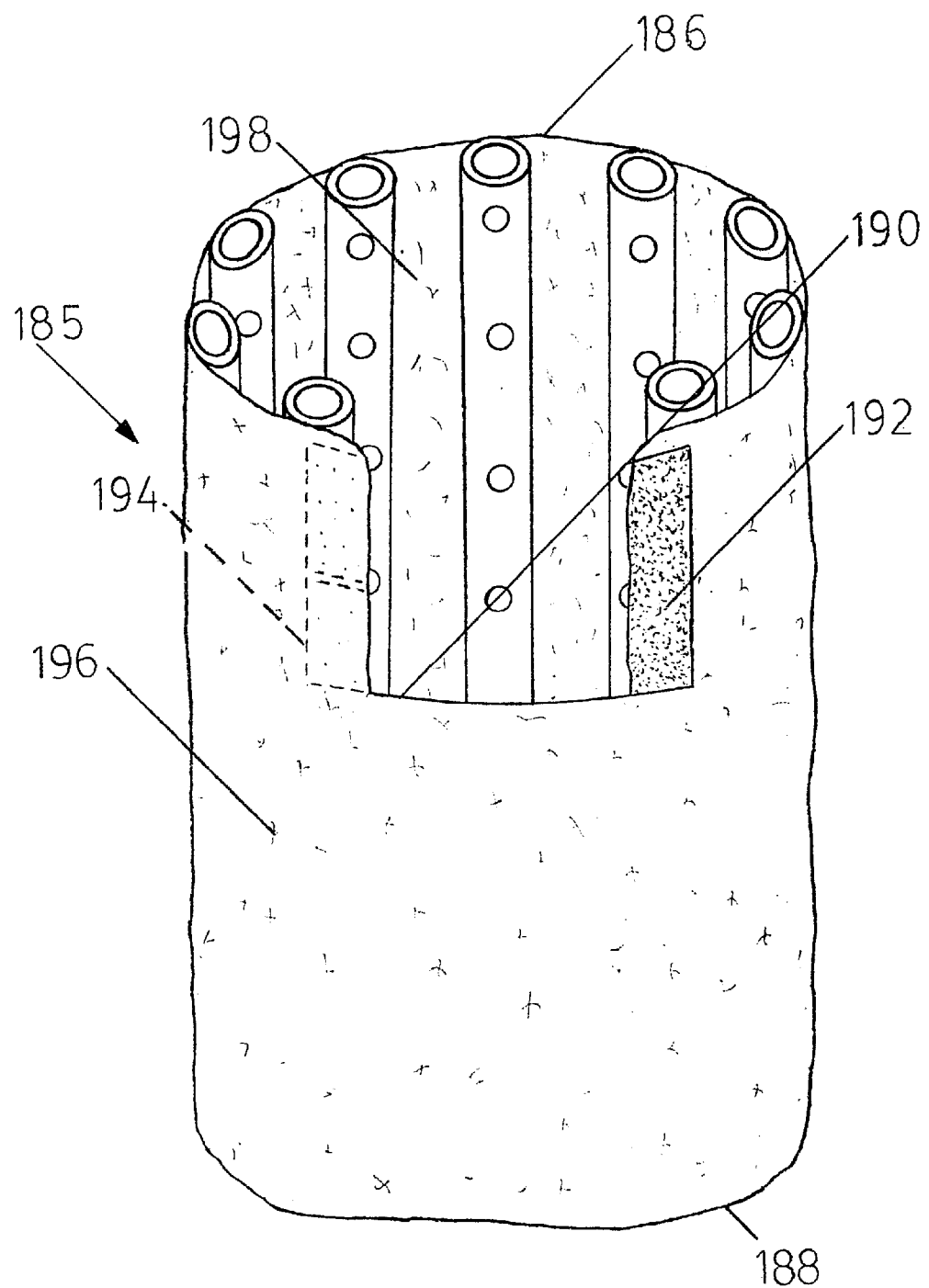
FIG. 21 is a perspective view illustrating yet another version of a cast venting device constructed in accordance with the invention, this version employing an opening that extends inwardly from one end of the venting device.

Yet another form of venting device is illustrated in FIG. 21, this device being indicated generally at 185. The venting device 185 is substantially tubular, at least for a substantial portion of its length. The device is open-ended at 186 and 188. However, extending longitudinally from one end, in this case the end 186, is an elongate slot or gap 190. The purpose of this gap is to make it easier to pull or draw this venting device over a limb or other body part by enabling the end 186 to be opened up to some extent. After this venting device has been put in place and arranged on the body part, the gap 190 can then be closed by means of hook and loop type flexible fastener strips indicated at 192 and 194. The strips 192 on the outer surface 196 of the venting device are preferably strips with hook like members distributed over the exposed or outer surface. Preferably the fastener strips 194 that are located on the inner surface 198 of the venting device are covered with numerous small loops in a well known manner. It will be appreciated that the gap 190 can thus be closed by simply connecting the loop strips 194 to the hook type fastener strips 192.

Figure 22:
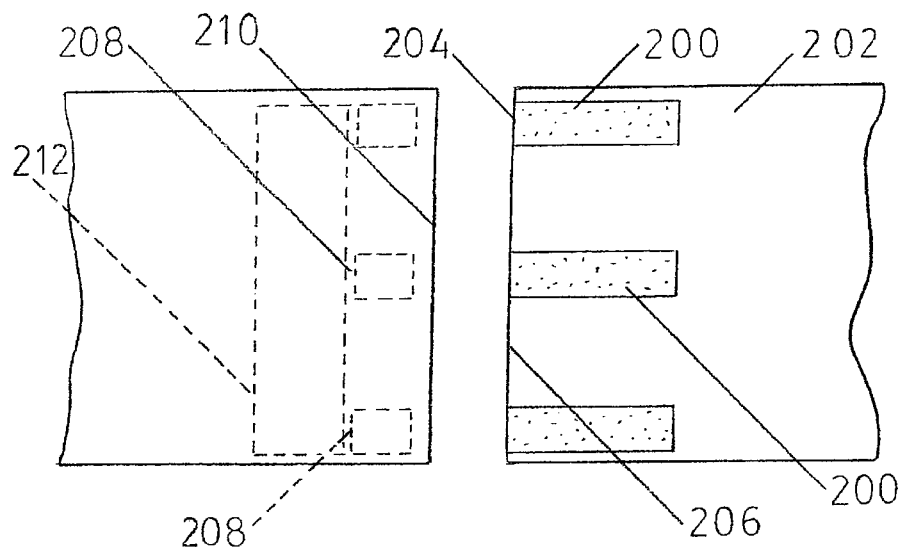
FIG. 22 is a detail view showing edge portions of a venting device similar to that illustrated in FIG. 20 but having a different arrangement for its flexible fastener strips.

FIG. 22 illustrates an alternative arrangement for the hook and loop type flexible fastener strips that can be used on the venting device, only a portion of which is shown. In the illustrated device, there are three hook-type fastener strips 200 affixed to an outer surface 202 of the fabric material that forms the venting device. An end 204 of each strip is positioned adjacent one of the side edges 206 of the flexible piece of fabric material. Thus, the three strips extend perpendicular to this side edge. Located on the inside surface of the fabric material are three square or rectangular loop type fasteners 208 which are outlined in dash lines. These fasteners 208 are arranged next to the opposite side edge 210 of the piece of fabric material. It will thus be seen that the diameter of the tube formed with the venting device having this arrangement can be adjusted simply by adjusting the position of each loop type fastener 208 relative to the hook type fastener strip 200. In order to provide for this form of flexibility and to avoid overlapping plastic tubes or aerating devices, a rectangular end region outlined in dash lines at 212 can initially be left without any tubular members or other aerating devices on the inner surface.

Figure 23:
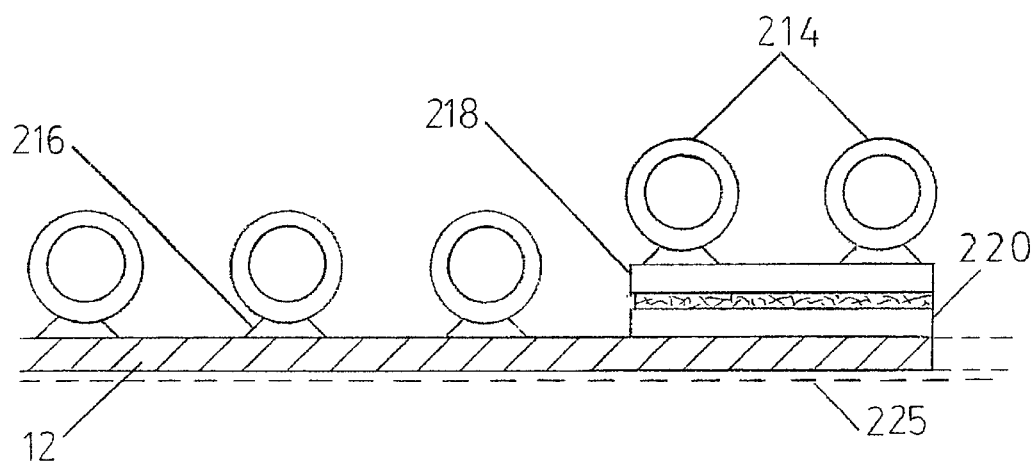
FIG. 23 is a detail edge view showing an optional feature of the venting device that enables aerating devices to be detachably connected to the fabric material.

Turning now to the optional feature illustrated in FIG. 23, it is shown in this figure how the aforementioned region 212 can be covered with plastic tubular members such as the two members 214 shown in FIG. 23. In particular, the two members 214 can be affixed by means of adhesive 216 to an outer surface of an elongate fastener strip 218. This fastener strip can be covered with a number of hook-type fasteners and can be of the aforementioned Velcro type. This strip can be detachably connected to a loop-type fastener strip 220 which can cover all or part of the region 212 on the inner surface of the venting device. The fastener strip 220 can be secured to the fabric material 12 in the usual manner, for example, by adhesive bonding or by stitching. It will be understood that this detachable tube arrangement can be used in any region or area on the inner surface of the venting device that may or may not require plastic tubular members or other aerating devices affixed thereto.

In order to prevent the material forming the cast from penetrating into the fabric material 12 and permanently bonding thereto and in order to make the venting device possibly reusable, it is possible to cover the venting device after it has been placed around the part of the human body to be covered in the cast with a thin plastic laminate that can be readily detached from the fabric material 12 when the surgical cast is later removed. The use of this optional plastic laminate 225 is indicated in dash lines in FIGS. 5 and 23. This laminate is quite flexible and bends readily to the contour of the outside surface of the venting device.

Another optional feature of the venting device is illustrated in FIG. 4. This feature is a short extension of the fabric material 12 at each end of the. fabric piece or tubular sleeve. This short extension is outlined in dash lines at 227. Inside of this extension there are no aerating devices or plastic tubular members. The purpose of this short extension is to permit the fabric material to be bent back around the edge of the hard cast material after the cast has formed and hardened. In this way, the softer fabric material 12 can help protect the user's skin at the end of the cast and make the cast more comfortable to wear.

Another advantageous optional feature that can be employed in the venting devices of the invention is that of making the fabric material 12 from threads or fibers having a distinctive color other than white or an off-white. Preferably the fabric material is made with a bright color such as green or blue. By making the fabric material with a color that is distinctively different from the white plaster of paris material that forms the hard cast, a medical technician or doctor removing the cast by means of a saw or other cutting tool will easily know when the tool has passed through the hard cast material and has contacted the venting device. This will be revealed by colored fibers being thrown out or removed by the cutting device. The technician or doctor will then know that it is not necessary to cut any deeper in that region of the cast. This feature lessens the risk of the patient being inadvertently cut by the cutting tool.

Preferably the venting device 10 of the invention is sterilized by a suitable sterilizing treatment after the device has been manufactured and prior to placement of the device into a suitable sealed package which maintains the device in a sterilized condition until it is to be used.

Various modifications and changes can be made to the described venting device of this invention without departing from the spirit and scope of this invention. Accordingly, all such modifications and changes as fall within the scope of the appended claims are intended to be part of this invention. For example, a gap or opening that can be closed by the use of hook and loop type fastener strips can be in a position other than that shown in FIG. 21 of the drawings. For example, there could be a longitudinally extending slot or gap formed in a central portion of a tubular venting device. The location of a gap or opening here may make the device easier to apply around a bent limb and may make it easier to conform the venting device to the shape of the limb or body part. For example, in the region of an elbow or knee that is bent, a suitable slot or opening can be provided on both sides of the venting device to properly accommodate both the outside bend and the inside corner of the bend. Once the venting device has been put in place, each opening can then be closed and the venting device properly fitted at the inside and outside corners using the hook and loop type fastener devices.

I claim:

1. A surgical cast venting device comprising:
    a stretchable single layer of porous fabric material having at least some elasticity and a flexible, tubular configuration, said fabric material having two opposite ends, which are open, and having an inner surface; and
    a substantial number of elongate plastic tubular members distributed over, adhesively bonded to, and located on said inner surface, said tubular members each being open-ended at both ends thereof and extending in a longitudinal direction relative to said fabric material, which has a length extending from one open end thereof to the opposite open end,
    wherein said venting device is adapted for placement around part of a human body or animal body prior to application of a surgical cast over said part of the body.

2. A venting device according to claim 1 wherein said fabric material has at least one strip of flexible fastener material having numerous small loop members formed thereon and at least another strip of flexible fastener material having numerous small hook members formed therein, said strips located on side edges of the fabric material and secured thereto and to one another in order to form said tubular configuration of the fabric material.

3. A venting device according to claim 1 wherein said fabric material is stockinet.

4. A venting device according to claim 3 wherein said tubular members are adhesively bonded to the fabric material by means of a medically acceptable adhesive which has been applied to an outer surface of the stockinet and has soaked through said fabric material to the plastic tubular members and which has been cured by exposure to ultraviolet light.

5. A surgical cast vending device comprising:
    a stretchable piece of porous fabric material having at least some elasticity and a flexible, tubular configuration, said piece having two opposite ends, which are open, and having an inner surface; and
    a substantial number of elongate, plastic tubular members distributed over, adhesively bonded to, and lobated on said inner surface, said tubular members each being open-ended at both ends thereof and extending in a lengthwise direction relative to said fabric material, which has a length extending from one open end thereof to the opposite open end, each plastic tubular member having at least several ventilation holes formed in the tubular side thereof and distributed along the length thereof,
    wherein said venting device is adapted for placement around part of a human body or animal body prior to application of a surgical cast over said part of the body.

6. A venting device according to claim 5 wherein said plastic tubular members extend substantially the length of said fabric material and each is located close to adjacent ones of the plastic tubular members.

7. A surgical cast venting device comprising:
    a stretchable piece of fabric material having at least some elasticity, having two opposite ends and two opposite side edges, and having inner and outer surfaces;
    plastic aerating devices affixed by adhesive bonding to and located on said inner surface, said aerating devices covering at least a major portion of said inner surface in a substantially uniform manner and comprising flexible layers of interconnected non-woven plastic threads, each layer having numerous, small air passageways formed therein and a substantially sponge-like appearance; and hook and loop type flexible fastener strips affixed to said fabric material, located at said two opposite side edges, and arranged for detachable connection to one another or flexible fastener strips on one or more similar venting devices in order to form said piece of fabric material into a tubular configuration or a portion of a tubular configuration, wherein said venting device is adapted for placement around part of a human body or animal body prior to application of a surgical cast over said part of the body.

8. A surgical cast venting device comprising:

a stretchable piece of fabric material having at least some elasticity, having two opposite ends and two opposite side edges, and having inner and outer surfaces;

plastic aerating devices affixed by adhesive bonding to and located on said inner surface, said aerating devices covering at least a major portion of said inner surface in a substantially uniform manner and comprising at least several corrugated plastic members each of which is perforated with a substantial number of small holes, said plastic members being distributed over said inner surface of the piece of fabric material; and hook and loop type flexible fastener strips affixed to said fabric material, located at said two opposite side edges, and arranged for detachable connection to one another or flexible fastener strips on one or more similar venting devices in order to form said piece of fabric material into a tubular configuration or a portion of a tubular configuration, wherein said venting device is adapted for placement around part of a human body or animal body prior to application of a surgical cast over said part of the body.

9. A surgical cast venting device comprising:

a stretchable piece of fabric material having at least some elasticity and a substantially tubular configuration, said piece having two opposite ends, and an inner surface, and at least several, separate elongate plastic tubular members distributed over and affixed to said inner surface, said tubular members each being open ended at at least one end and having at least several ventilation holes formed in the tubular side thereof, said tubular members extending substantially from one of said opposite ends to the other of said opposite ends, wherein said venting device is adapted for placement around part of a human body or animal body prior to application of a surgical cast over said part of the body.

10. A venting device according to claim 9 wherein said plastic tubular members are adhesively bonded to said piece of fabric material and each plastic tubular member is located close to but spaced apart from adjacent ones of the plastic tubular members.

11. A venting device according to claim 10 wherein said piece of fabric material is porous stockinet.

12. A venting device according to claim 11 wherein said tubular members are adhesively bonded to the fabric material by means of a medically acceptable adhesive which has been applied to an outer surface of the stockinet and has soaked through said fabric material to the plastic tubular members and which has been cured by exposure to ultraviolet light.

13. A venting device according to claim 10 wherein said venting device has been placed around said part of the human body and the piece of fabric material is substantially covered by a thin plastic laminate that can be readily detached from said piece of fabric material when the surgical cast is later removed.

* * * * *